US009023350B2

(12) United States Patent
Gallo Barraco (10) Patent No.: US 9,023,350 B2
(45) Date of Patent: May 5, 2015

(54) SYNERGISTIC PHARMACEUTICAL COMPOSITION USEFUL FOR INHIBITING CORNEAL AND RETINAL NEOVASCULARIZATION (ANGIOGENESIS), AND IN OTHER ORGANS, IN A HUMAN BEING OR ANIMALS (75) Inventor: Juan Eduardo María Gallo Barraco, Buenos Aires (AR)

(73) Assignee: Association Civil de Estudios Superiores, Ciudad de Buenos Aires (AR)

( * ) Notice: Subject to any disclaimer, the term of this patent is extended or adjusted under 35 U.S.C. 154(b) by 1217 days.

(21) Appl. No.: 12/735,659

(22) PCT Filed: Aug. 7, 2008

(86) PCT No.: PCT/MX2008/000104
§ 371 (c)(1),
(2), (4) Date: Dec. 2, 2010

(87) PCT Pub. No.: WO2009/022897
PCT Pub. Date: Feb. 19, 2009

(65) Prior Publication Data
US 2011/0076266 A1    Mar. 31, 2011

(30) Foreign Application Priority Data
Aug. 7, 2007 (AR) .................. P070103482

(51) Int. Cl.
*A61K 39/395* (2006.01)
*A61K 31/185* (2006.01)
*A61K 45/06* (2006.01)
*C07K 16/22* (2006.01)
*C07C 309/35* (2006.01)
*C07C 309/47* (2006.01)
*A61K 31/167* (2006.01)

(52) U.S. Cl.
CPC ............. *A61K 31/185* (2013.01); *C07C 309/35* (2013.01); *C07C 309/47* (2013.01); *A61K 31/167* (2013.01); *A61K 39/3955* (2013.01); *A61K 45/06* (2013.01); *C07K 16/22* (2013.01)

(58) Field of Classification Search
CPC ....... A61K 31/04; A61K 31/10; A61K 31/13; A61K 31/15; A61K 31/165; A61K 31/166; A61K 31/167; A61K 31/17; A61K 39/395; A61K 39/39533; A61K 39/3955; A61K 2039/505; C07C 15/24; C07C 2102/10; C07C 205/04; C07C 225/16; C07C 275/28; C07C 309/28; C07C 309/34; C07C 309/35; C07C 309/47; C07K 16/22; C07K 16/461; C07K 16/464; C07K 16/465
USPC .......................................................... 514/54
See application file for complete search history.

(56) References Cited

U.S. PATENT DOCUMENTS 6,121,320 A     9/2000  Doukas
8,598,221 B2   12/2013  Girard et al.
2007/0071756 A1  3/2007  Peyman

FOREIGN PATENT DOCUMENTS

WO    2006/125815    11/2006

OTHER PUBLICATIONS

Lopez, E.S., et al., ARVO Meeting Abstracts in: Invest. Ophthalmol. Vis. Sci., 48: 1717, 2007, May.*
Kruse, F.E., et al., Vision Res. 35: S94, Abstract No. 2216, 1995.*
V. E Klepeis et al., "P2Y Receptors Play a Critical Role in Epithelial Cell Communication and Migration," Journal of Cellular Biochemistry, 2004, vol. 93, pp. 1115-1133.
J. E. Gallo et al., "Suramin Inhibits Experimental Retinal Neovascularization. Possible Role of Purinergic P2 Receptors," Invest Ophthalmol Vis Sci, 2006, vol. 47, p. 3224.
M. P. Abbracchio et al., "Purinoceptors: Are There Families of P2X and P2Y Purinoceptors," Pharmac. Ther., 1994, vol. 64, pp. 445-475.
Y. Li et al., "Müller Cell $Ca^{2+}$ Waves Evoked by Purinergic Receptor Agonists in Slices of Rat Retina," Journal of Neurophysiology, 2001, vol. 85, pp. 986-994.
T. Fujihara et al., "Improvement of Corneal Barrier Function by the $P2Y_2$ Agonist INS365 in a Rat Dry Eye Model," Investigative Ophthalmology and Visual Science, Jan. 2001, vol. 42, No. 1, pp. 96-100.
S. Uhlmann et al. "Early Glial Cell Reactivity in Experimental Retinal Detachment: Effect of Suramin," Investigative Ophthalmology and Visual Science, Sep. 2003, vol. 44, No. 9, pp. 4114-4122.
K. Muthusamy Kathir et al., "Understanding the Mechanism of the Antimitogenic Activity of Suramin," Biochemistry, 2006, vol. 45, pp. 899-906.
L. G. Presta et al., "Humanization of an Anti-Vascular Endothelial Growth Factor Monoclonal Antibody for the Therapy of Solid Tumors and Other Disorders," Cancer Research, 1997, vol. 57, pp. 4593-4599.
M. Saunders et al., "Management of advanced colorectal cancer: state of the art," British Journal of Cancer, 2006, vol. 95, pp. 131-138.
F. Bock et al., "Bevacizumab as a Potent Inhibitor of Inflammatory Corneal Angiogenesis and Lymphangiogenesis," Investigative Ophthalmology and Visual Science, Jun. 2007, vol. 48, No. 6, pp. 2545-2552.

(Continued)

*Primary Examiner* — Misook Yu
*Assistant Examiner* — Anne Holleran
(74) *Attorney, Agent, or Firm* — Jacobson Holman, PLLC.

(57) ABSTRACT

A synergistic pharmaceutical composition useful for inhibiting corneal and retinal neovasculization (angiogenesis) and in other organs, in a human being or animal, characterized in comprising, in a pharmaceutically acceptable vehicle or carrier: 60 to 90 weight % Suramine, or the equivalent of one of the pharmaceutically acceptable salts thereof; and 40 to 10 weight % Bevacizumab; wherein said percentages are relative to the addition of weight of both active principals. Said synergistic pharmaceutical composition is under the form of an injectable composition by intravenous, intravitrea or subconjuntival means or under the form for topical administration.

5 Claims, 5 Drawing Sheets

(56) References Cited

OTHER PUBLICATIONS

J. DeStefano et al., "Topical bevacizumab therapy for corneal neovascularization," Arch Ophthalmol, 2007, vol. 125, pp. 834-836.
E. S. Lopez et al., "Effect of Bevacizumab (Avastin) and Suramin in a Rabbit Model of Corneal Neovascularization," Invest Ophthalmol Vis Sci, 2007, vol. 48, 2 pgs.
C. Cursiefen et al., "Inhibition of Hemangiogenesis and Lymphangiogenesis after Normal-Risk Corneal Transplantation by Neutralizing VEGF Promotes Graft Survival," Investigative Ophthalmology and Visual Science, Aug. 2004, vol. 45, No. 8, pp. 2666-2673.
M. Zheng et al,. "Control of Stromal Keratitis by Inhibition of Neovascularization," American Journal of Pathology, Sep. 2001, vol. 159, No. 3, pp. 1021-1029.
M. A. Villalona-Calero et al., "Phase I Study of Low-Dose Suramin as a Chemosensitizer in Patients with Advanced Non-Small Cell Lung Cancer," Clinical Cancer Research, Aug. 15, 2003, vol. 9, pp. 3303-3311.
H. Schmoll et al. "Single agent fluorouracil for first-line treatment of advanced colorectal cancer as standard," Lancet, 2007, vol. 370, pp. 105-107.
M. Koopman et al., "Sequential versus combination chemotherapy with capecitabine, irinotecan, and oxaliplatin in advanced colorectal cancer (CAIRO): a phase III randomized controlled trial," Lancet, Jul. 14, 2007, vol. 370, pp. 135-142.
S. Ramaswarmy, "Rational Design of Cancer-Drug Combinations," The New England Journal of Medicine, Jul. 19, 2007, vol. 357, No. 3, pp. 299-300.
M. T. Seymour et al., "Different strategies of sequential and combination chemotherapy for patients with poor prognosis advanced colorectal cancer (MRC FOCUS): a randomized controlled trial," Lancet, Jul. 14, 2007, vol. 370, pp. 143-152.
J. E. Gallo et al., "A Population-Based Study of Ocular Abnormalities in Premature Children Aged 5 to 10 Years," American Journal of Ophthalmology, May 1991, vol. 111, pp. 539-547.
A. J. Augustin et al., "Triple Therapy for Choroidal Neovascularization due to Age-Related Macular Degeneration," Retina, 2007, vol. 27, No. 2, pp. 133-140.
M. D. Rabena et al., "Intravitreal Bevaciuzumab (Avastin) in the Treatment of Macular Edema Secondary to Branch Retinal Vein Occlusion," Retina, 2007, vol. 27, No. 4, pp. 419-425.
F. Bock et al., "Bevacizumab as a Potent Inhibitor of Inflammatory Corneal Agniogenesis and Lymphangiogenesis," Investigative Ophthalmology and Visual Science, Jun. 2007, vol. 48, No. 6, pp. 2545-2552.
M. Erdurmus et al., "Subconjunctival bevacizumab for corneal neovascularization," Graefe's Arch Clin Exp Ophthalmol, 2007, vol. 245, pp. 1577-1579.
S. Sarman et al., "Involvement of Purinegic P2 Receptors in Experimental Retinal Neovascularization," Current Eye Research, Mar. 1, 2008, vol. 3, No. 3, pp. 285-291.
S. C. Brodovsky et al., "Management of Alkali Burns: An 11 Year Retrospective Review," American Academy of Ophthalmology, 2000, vol. 107, No. 10, pp. 1829-1835.
H.S. Dua et al., "Stem cell differentiation and the effects of deficiency," Eye, 2003, vol. 17, pp. 877-885.
P. Garg et al., "The value of corneal transplantation in reducing blindness," Eye, 2005, vol. 19, pp. 1106-1114.
E. R. Lazarowski et al., "Mechanisms of Release of Nucleotides and Integration of Their Action as P2X- and P2Y-Receptor Activating Molecules," Molecular Pharmacology, 2003, vol. 64, pp. 785-795.
J. E. Fries et al., "Identification of P2Y Receptor Subtypes in Human Müller Glial Cells by Physiology, Single Cell RT-PCR, and Immunohistochemistry," Investigative Ophthalmology and Visual Science, Aug. 2005, vol. 46, No. 8, pp. 3000-3007.
L. Wang et al., "P2 Receptor Expression Profiles in Human Vascular Smooth Muscle and Endothelial Cells," Journal of Cardiovascular Pharmacology, 2002, vol. 40, pp. 841-853.
K. Morigiwa et al., "P2 purinoceptor expression and functional changes of hypoxia-activated cultured rat retinal microglia," Neuroscience Letters, 2000, vol. 282, pp. 153-156.
A. Yanyali et al., "Bevacizumab (Avastin) for Diabetic Macular Edema in Previously Vitrectomized Eyes," American Journal of Ophthalmology, Jul. 2007, pp. 124-126.
G. Bocci et al., "Inhibitory effect of suramin in rat models of angiogenesis in vitro and in vivo," Cancer Chemother Pharmacol, 1999, vol. 43, pp. 205-212.
J. F. Arevalo et al., "Primary Intravitreal Bevacizumab (Avastin) for Diabetic Macular Edema," American Academy of Ophthalmology, 2007, vol. 114, No. 4, pp. 743-750.
R. Lazic et al., "Verteporfin Therapy and Intravitreal Bevacizmab Combined and Alone in Choroidal Neovascularization due to Age-Related Macular Degeneration," American Academy of Ophthalmology, 2007, vol. 114, No. 6, pp. 1179-1185.
T. E. Hutson et al., "Targeting Growth Factor and Antiangiogenic Pathways in Clear-Cell Renal Cell Carcinoma: Rationale and Ongoing Trials," Clinical Genitourinary Cancer Supplement, Dec. 2006, vol. 5, Suppl. 1, pp. S31-S39.

\* cited by examiner

SYNERGISTIC PHARMACEUTICAL COMPOSITION USEFUL FOR INHIBITING CORNEAL AND RETINAL NEOVASCULARIZATION (ANGIOGENESIS), AND IN OTHER ORGANS, IN A HUMAN BEING OR ANIMALS

This is a national stage of PCT/MX08/000104 filed Aug. 7, 2008 and published in Spanish, which has a priority of Argentina no. P 20070103482 filed Aug. 7, 2007, hereby incorporated by reference.

FIELD OF THE INVENTION

Suramine (suramin) is a drug that has been known for many years for treating illnesses caused by nematodes and protozoon. Its properties as an anti-neoplasic agent have also been described through various mechanisms: tumor angiogenesis inhibition, increase of cellular sensitivity to cytotoxic substances (chimiotherapy) and cytotoxic action itself.

Suramine can de chemically named as 8-[[4-methyl-3-[[3-[[3-[[2-methyl-5-[(4,6,8-trisulphonaphthalene-1-yl)carbamoyl]phenyl]carbamoyl]phenyl]carbamoyl]-amino]benzoyl]amino]naphthalene-1,3,5-trisulphonic acid, the empiric formula being $C_{51}H_{40}N_6O_{23}S_6$ and number CAS 145-63-1.

Bevacizumab, a biologically active substance known for its anti-VEGF (vascular endothelial growth factor) effect, inhibits angiogenesis. Is used for colon cancer for its antiangiogenic effect by diminishing tumor growth and for treatment of ophthalmic illnesses that develop neovasculization, such as diabetic retinopathy, macular degeneration related to exudative-type age and others.

Recently, Bevacizumab has been used in ophthalmology as an intravitreo agent for treating proliferative eye illnesses (neovasculization). Furthermore, has been approved as a new suggestion for treatment of mammary cancer in many countries Unexpected and surprisingly a new pharmaceutical composition has been found comprising Suramine y Bevacizumab (from now on named suramab) administrated at relatively low doses has a great antiangiogenic effect, synergistic like, with greater intensity and longer duration than the effect produced by a mono-doses of Bevacizumab or Suramine.

BRIEF DESCRIPTION OF THE INVENTION

Medical Aspects

A) Corneal Angiogenesis

The objective of the present invention is to provide pharmaceutical composition comprising Suramine, non-specific purinergic antagonist, and Bevacizumab, anti-VEGF substance, in the development of corneal angiogenesis.

With this in mind a well known method was used to induce neovasculization on the cornea. Appearance of neoformation vessels in the cornea was documented with a digital camera during a period of 35 days. Suramab's (Suramina+Bevacizumab) effect on animals was compared with that of three other groups of animals treated with Bevacizumab, treated with Suramine and without any type of treatment (control group).

Suramab administrated intravenously, notably diminished development of neovessels on the cornea and had significantly higher and longer effect than that of the other groups of animals during 35 days of evaluation. Results have revealed that suramab has a noticeable antiangiogenic effect, capable of stopping corneal neovasculization and in other places of the organism, constituting a new pharmacological agent for antiangiogenic treatment.

B) Tumor Angiogenesis

Another objective of the present invention is to provide a pharmaceutical composition comprising non-specific purinergic antagonist Suramine and anti-VEGF substance Bevacizumab, in the development of tumor angiogenesis and on the survival of experimental animals.

With this in mind a well known animal model was used. Briefly, CT26 cells (colon adenocarcinoma) were inoculated, subcutaneously, in the dorsal-lateral region of rats. On the 7th day of inoculation 4 groups of animals were formed that received different treatments intravenously: suramab, bevacizumab, suramine, physiological solution (control). The tumors were measured three times a week, the tumor volume was calculated following a known formula and survival of animals was evaluated. The treated groups were compared to the control group.

Only the group treated with suramab has a statistically significant decrease in the tumor volume at day 31 relative to the control group. Also, it is the group that has the biggest survival percentage at day 35.

DETAILED DESCRIPTION OF THE FIGURES

DETAILED DESCRIPTION OF THE INVENTION

I. Angiogenesis

I.1.—Introduction

The cornea, located in the front part of the eye, is a transparent and avascular tissue. Some ocular pathology can cause loss of its avascularity and transparency, producing decrease or loss of vision. It is estimated that in the United States, a million and a half patients develop corneal neovasculization, some of them with loss of vision, named corneal blind patients (Brodovsky S C, McCarty C A, Snibson G, Loughnan M, Sullivan L, Daniell M, Taylor H R. Management of alkali burns: an 11-year retrospective review. Ophthalmology. 2000; 107: 1829-35). The most frequent causes of invasion of vessels on the cornea (corneal neovasculization) are: ocular infections such as simple herpes virus, aftermath of illnesses such as Pemphigus and Steven Johnson Syndrome, giant Pterigion, and specially alkali burns. The pathologies mentioned run their course with severe damage or destruction of corneal limbo truncal cells (stem cells), which should not allow entrance of blood vessels through the corneal periphery (Dua H S, Joseph A, Shanmuganathan V A, Jones R E. Stem cell differentiation and the effects of deficiency. Eye 2003; 17:877-85).

Handling of corneal neovasculization continues to be complex, although advances have been achieved in the treatment of this pathology. Cases that could benefit from a conventional corneal transplant have a bad prognosis owing to frequent recurrence of neovasculization. Experience demonstrates that it is necessary to significantly diminish neovasculization before performing a conventional corneal transplant (Garg P, Krishna P V, Stratis A K, Gopinathan U. The value of corneal transplantation in reducing blindness. Eye. 2005; 19:1106-14).

New treatments such as e.g. transplant of corneal limbo stem cells are at an initial stage of development. However, in the few reported cases it is not rare to find recurrence of corneal neovasculization.

Cell surface receptors for extracellular nucleotides are named receptors P2. These are activated by nucleotides such as purynes and/or pyrimidines. Receptors P2 are divided in two big groups: P2X and P2Y. Receptors P2X are involved in ion flow control in the cell in response to ATP (adenosine triphosphate). Receptors P2X participate in rapid neurotransmission and are found in great quantities in tissues having an excitation function. Subtypes P2X1, P2X2, P2X3, etc., are described in bibliography. Receptors P2Y belong to the family of receptors coupled to Protein a G, and various types have also been found such as P2Y1, P2Y2, etc. (Abbracchio M P, Burnstock G. Purinoceptors: are there families of P2X and P2Y purinoceptors? Pharmacol Ther 1994; 64:445-75).

Receptors P2 are present in glial cells in the retina and also in the cornea (Lazarowski E, Boucher R, Harden T. Mechanisms of release of nucleotides and integration of their action as P2X- and P2Y-receptor activating molecules. Mol Pharmacol 2003; 64 (4):785-95; Fries J E, Goczalik I M, Wheeler-Schilling T H, Kohler K, Guenther E, Wolf S, Wiedeman P, Bringmann A, Reichenbach A, Francke M, Pannicke T. Identification of P2Y receptor subtypes in human Muller glial cells by physiology, single cell RT-PCR, and immunohistochemistry. Invest Ophthalmol Vis Sci. 2005 August; 46 (8): 3000-7; Wang L, Karlsson L, Moses S, Hultgardh-Nilsson A, Andersson M, Borna C, Gudbjartsson T, Jern S, Erlinge D. P2 receptor expression profiles in human vascular smooth muscle and endothelial cells. J Cardiovasc Pharmacol 2002 December; 40 (6): 841-53; Li Y, Holtzclaw L A, Russell J T. Muller cell Ca2+ waves evoked by purinergic receptor agonists in slices of rat retina. J Neurophysiol 2001 February; 85 (2): 986-94; Fujihara T, Murakami T, Fujita H, Nakamura M, Nakata K. Improvement of corneal barrier function by the P2Y(2) agonist INS365 in a rat dry eye model. Invest Ophthalmol V is Sci. 2001 January; 42 (1): 96-100). Retinal illnesses have been found to be activated with a greater immunoreactivity (Morigiwa K, Quan M, Murakami M, Yamashita M, Fukuda Y. P2 Purinoceptor expression and functional changes of hypoxia-activated cultured rat retinal microglia. Neurosci Lett. 2000; 282:153-6). Experimental studies in animals on retinal detachment demonstrated a positive immunoreactivity of receptors P2Y2 specially in the internal layers of the retina, achieving a clear identification thereof in glial cells such as astrocytes and Muller cells. However, after 7 days of retinal detachment evolution receptor P2Y2 already expressed itself in other parts of the retina (Uhlmann S, Bringmann A, Uckermann O, Pannicke T, Weick M, Ulbricht E, Goczalik I, Reichenbach A, Wiedemann P, Francke M. Early glial cell reactivity in experimental retinal detachment: effect of suramin. Invest Ophthalmol V is Sci. 2003 September; 44 (9): 4114-22).

Suramine acts by blocking purinergic receptors. However, has also been found blocking other receptors of angiogenic molecules such as FGF and VEGF (Kathir K M, Kumar T K, Yu C. Understanding the mechanism of the antimitogenic activity of suramin. Biochemistry. 2006 Jan. 24; 45 (3): 899-906).

VRGF's (vascular endothelial growth factor) role is broadly known in angiogenisis in different parts of the human body. Bevacizumab (rhuMAb VEGF) is a monoclonal antibody, humanized and recombinant, that binds to VEGF-A preventing action thereof on the corresponding receptor and in this way inhibiting angiogenesis (Presta L, Chen H, O Connor S, et al. Humanization of an antivascular endothelial growth factor monoclonal antibody for the therapy of solid tumors and other disorders. Cancer Res 1997; 57: 4593-4599). It is used in combined chemotherapy for treating colon cancer, preventing tumor growth owing to its angiostatic effect (Saunders M, Iveson T. Management of advanced colorectal cancer: state of the art. BMJ 2006, 95:131-38). It has been authorized in our country with this suggestion (1996-2006, Productos Roche S.A.Q. e I., Buenos Aires). It is Currently used in ophthalmology for treating illnesses than run their course with retinal neovasculization and are frequent blindness causes such as macular degeneration related to exudative-type age and diabetic retinopathy. In addition, recent investigations point out the possibility of use for corneal neovasculization (Bock F, Onderka J, Dietrich T, Bachmann B, Kruse F, Paschke M, Zahn G, Cursiefen C. Bevacizumab as a potent inhibitor of inflammatory corneal angiogenesis and lymphangiogenesis. Invest Ophthalmol V is Sci 2007; 48: 2545-2552; DeStafeno J, Kim T. Topical bevacizumab therapy for corneal neovascularization. Arch Ophthalmol 2007; 125: 834-836).

To the publication of other investigators are added pieces of work performed in our institution according to which monodoses of Bevacizumab and monodoses of Suramine reduce corneal and retinal neovasculization (Gallo J E, Sarman S, Mancini J, van der Ploeg I, Croxatto J O, Kvanta A. Suramin Inhibits Experimental Retinal Neovascularization. Possible Role of Purinergic P2 Receptors. Invest. Ophthalmol. Vis. Sci. 2006 47: E-Abstract 3224, Lopez E, Croxatto J O, Kvanta A, Gallo J E. Effect of Bevacizumab (Avastin) and Suramin in a Rabbit Model of Corneal Neovascularization. Invest. Ophthalmol. Vis. Sci. 2007 48: E-Abstract 1717). Based on these facts we proposed to evaluate suramab effectiveness, (a pharmaceutical composition comprising Suramine and Bevacizumab) to inhibit corneal angiogenesis in a corneal neovasculization classical animal model (Fujihara T, Murakami T, Fujita H, Nakamura M, Nakata K. Improvement of corneal barrier function by the P2Y(2) agonist INS365 in a rat dry eye model. Invest Ophthalmol V is Sci. 2001 January; 42 (1): 96-100; Klepeis V E, Weinger I, Kaczmarek E, Trinkaus-Randall V. P2Y receptors play a critical role in epithelial cell communication and migration. J Cell Biochem. 2004 Dec. 15; 93 (6): 1115-33; Cursiefen C, Cao J, Chen L et al. Inhibition of hem and lymphangiogenesis after normal-risk corneal transplantation by neutralising VEGF promotes graft survival. Invest Ophthalmol V is Sci 2004; 45: 2666-2673) and angiogenesis associated to cancer in the animal model using colon adenocarcinoma cells.

II.2.—Examples

II.2.1.—Materials and Methods

Corneal Neovasculization Model

After anaesthetizing a Newzealender breed white rabbit of 3 kg. with a midazolam and ketamine hydrochloride with an intramuscular injection, installation of topical proparacaine was performed (Anestalcon, Alcon, Argentina) in the eye and a blepharostat was place on the right eye. During 20 seconds 7 mm diameter dicks of Whatman filter paper were soaked in a 1N NaOH solution. The paper disk was placed on the central part of the cornea with a pincer leaving it there for 2 minutes. Immediately afterwards the injured zone was washed with 15 ml saline physiological solution (ClNa, 0.9%) during one minute. The same process was performed on 12 rabbits of the same color, breed and weight.

Neovasculization Result (Score)

Formation of neovessels were quantified with a value of 0 to 4 to each quadrant according to the centripetal growth of the longest vessel (in 1 mm increases i.e, 0=0 mm; 1=equal or less than 1 mm; 2=more than 1 and up to 2 mm; 3=more than 2 and up to 3 mm; 4=more than 3 mm). The sum of the four quadrants provided the neovasculization index (INV) for that eye. The measurement of the vessels was performed on the digital images taken with a Nikon Coolpix 5700 Digital Camera (Nikon, Tokyo, Japan) at days 9, 15, 21 and 35 after the lesion (Zheng M, Schwarz M A, Lee S, Kumaraguru U, Rouse B T. Control of stromal keratitis by inhibition of neovascularization. Am J. Pathol. 2001 September; 159 (3): 1021-9).

Monodoses Administration of Suramine, Bevacizumab and Suramab

Thirty minutes after causing the corneal lesion 20 mg/kg of suramine hexa-sodium (Biomol International, PA, USA) dissolved in 5 ml saline physiological solution (ClNa 0.9%) was injected through an intravenous infusion pump for 20 minutes. Bevacizumab (Roche, Buenos Aires, Argentina) was administrated in the same manner in a doses of 5 mg/kg dissolved in 5 ml saline physiological solution (ClNa, 0.9%). A solution of suramab, composed by Bevacizumab (3 mg/kg) and Suramine hexa-sodium (10 mg/kg) in 5 ml saline physiological solution (ClNa, 0.9%) was administrated intravenously in the same manner. Therefore, four groups were formed with three animals each: one group treated with Suramine, one group treated with Bevacizumab, one group treated with suramab and the remaining group without any treatment (control group).

The suramab solution was obtained by the following process: 30 mg Suramine hexa-sodium were dissolved in 4.64 ml saline physiological solution (NaCl, 0.9%) by continuous shaking for 4 minutes.

9 mg Bevacizumab (0.36 ml from a 100 mg/4 ml Avastin ampoule, Roche, Buenos Aires, Argentina) were added to the Suramine solution previously prepared, and the 5 ml of the resulting mixture was kept under refrigeration at 4° C. until application.

The resulting suramab was injected with a butterfly catheter channeling the auricular vein and by slow intravenous perfusion for 15 to 20 minutes.

Post-Operation Control 24 hs after the lesion was caused the first clinical examination was performed and was then continued every three days. This was carried out using an operator microscope or a surgical magnifying glass and photographs were taken with a digital camera Nikon Coolpix 5700. The INV register was performed on days 9, 15, 21 and 35 on all the animals. The average INV of each group was used to carry out the comparative analysis.

Oncological Angiogenesis Model $5 \times 10^5$ CT26 cells (colon adenocarcinoma) were inoculated subcutaneously, in the dorsal-lateral region of Balb/c rats. On the 7th day of inoculation 4 groups of animals were formed that received different treatments via iv (in the tail vein).

Suramin, Bevacizumab and Suramab Monodoses Administration a. Bevacizumab group: (n=10), 5 mg/Kg (1 rat=30 g, approx. 0.15 mg per rat) in 100 µl of physiological solution (PS) under slow infusion.
b. Suramine group: (n=10) 20 mg/Kg (1 rat=30 gr, approx. 0.6 mg per rat) in 100 µl PS under slow infusion.
c. Suramab group: (n=10), Suramine 20 mg/Kg+Bevacizumab 5 mg/Kg (approx. 0.6 g suramine and 0.15 mg Bevacizumab per rat) in 100 µl PS under slow infusión
d. Control group: (n=7) PS 100 µl under slow infusion.

Post-Operation Control

The tumors were measured three times per week. The following formula was used to calculate the tumor volume: (larger diameter+smaller diameter squared)/2. The animals having tumors volumes greater or equal to 8000 mm3 were sacrificed.

Survival was considered till day 35 post tumor inoculation.

2.2.2.—Results

Corneal Neovasculization

The results obtained for the four groups of animals is shown in the following table:

TABLE 1

| | NEOVASCULIZATION INDEX AVERAGE | | | |
|---|---|---|---|---|
| | DAY 9 | DAY 15 | DAY 21 | DAY 35 |
| BEVACIZUMAB | 1 | 4 | 5 | 12 |
| SURAMINE | 4 | 6 | 7 | 7 |
| SURAMAB | 0 | 0.7 | 1.3 | 1.7 |
| CONTROL | 7 | 11 | 13 | 15 |

Bevacizumab, Suramine and suramab had an inhibiting effect on neovasculization during 35 days.

Figure 1:
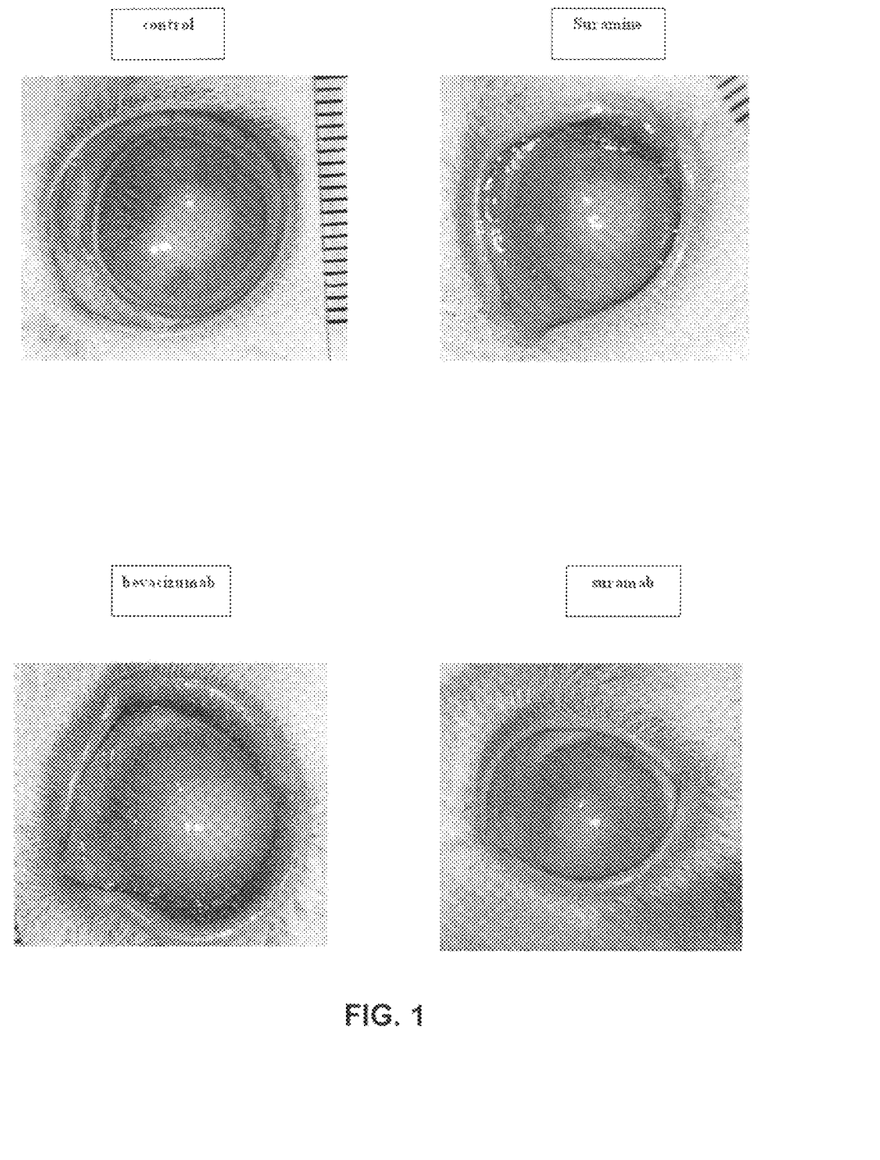
FIG. 1 illustrates the development of corneal neovessels 21 days after lesion: A) control; B) Bevacizumab; C) Suramine; D) suramab.
Figure 2:
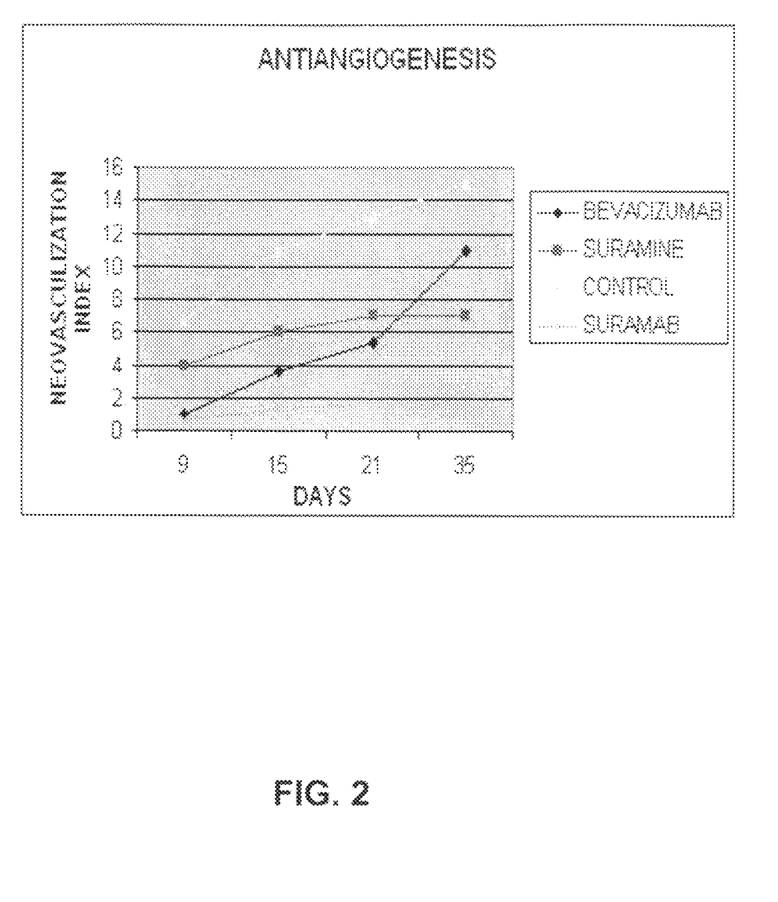
FIG. 2 shows evolution of neovessels (neovasculization index) versus length of time (days) of the test for the four groups of animals.

However, as may be clearly noticed in the Table 1 as well as FIGS. 1 and 2, application of suramab has significantly bigger and synergistic effect on the degree of neovessels inhibition for 35 days of evaluation.

According to the preceding experimental results, the proposed invention refers to a synergistic pharmaceutical composition, useful for inhibiting corneal and retinal neovasculizationla (angiogenesis) and in other organs, in a human being or animal, comprising, in a pharmaceutically acceptable vehicle or carrier:

60 to 90 weight % Suramine, or the equivalent of one pharmaceutically acceptable salt thereof; and 40 to 10 weight % Bevacizumab;

wherein said percentages are relative to the addition of weight of both active principals.

More preferably, instant application refers to a synergistic pharmaceutical composition useful for inhibiting corneal and retinal neovasculization and in other organs, in a human being or animal, comprising in a pharmaceutically acceptable vehicle or carrier:

approximately 75 weight % Suramine, or the equivalent of one of the pharmaceutically acceptable salts thereof; and approximately 25 weight % Bevacizumab;

wherein said percentages are relative to addition of weight of both active principals.

Even more preferably, the present invention refers to an injectable synergistic pharmaceutical composition useful for inhibiting corneal and retinal neovasculization and in other organs, in a human being or animal, comprising:

approximately 0.18 weight % Suramine, or the equivalent of one of the pharmaceutically acceptable salts thereof; and approximately 0.06 weight % Bevacizumab; the rest being a pharmaceutically acceptable vehicle or carrier wherein the percentages have been given relative to the pharmaceutical composition total weight.

Preferably, in these injectable synergistic pharmaceutical compositions, 0.18 weight % Suramina was found under the form of a hexa-sodium salt thereof.

Finally, the compositions of the present invention are considered to be under the pharmaceutical form of an injectable composition by intravenous, intravitrea or subconjuntival means or for topical administration.

Angiogenesis (Neovasculization) Associated to Oncological Illnesses

The tumor volume growth is known to be related to the greater or less vasculization of the tumor, by which the tumour cells are nourished. In our experimental test Bevacizumab, Suramine and suramab had an inhibiting effect on tumor neovasculization (angiogenesis) during the 31 days, shown by a reduction of tumor volume compared to the control group. However, only suramab produced a statistically significant reduction.

It is also important to point out that the survival percentage was greater in animals treated with suramab on day 35.

Figure 3:
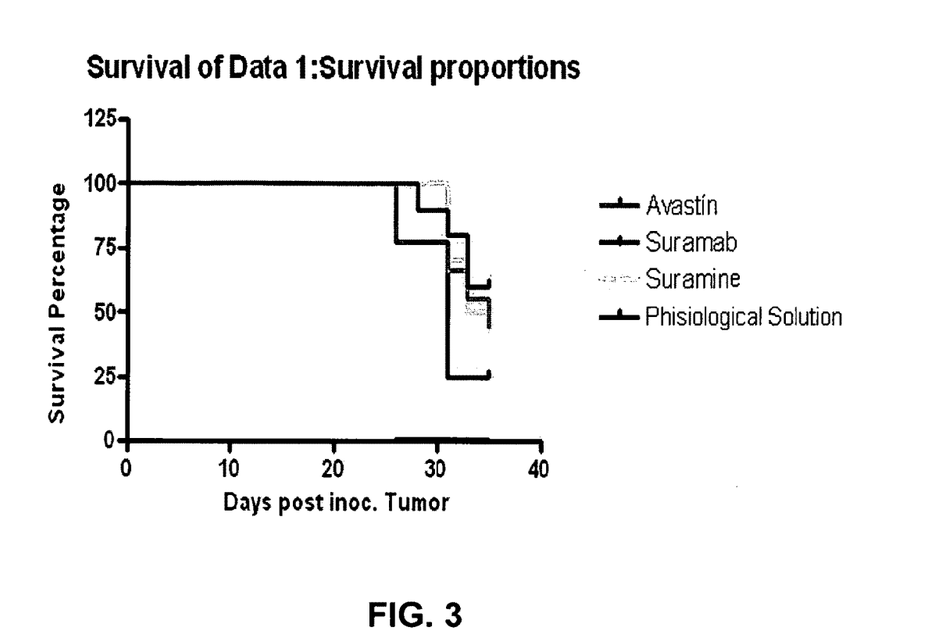
FIG. 3 illustrates the survival percentage in the length of time (days) of the test of the oncological angiogenesis model for the four groups of animals up to day 35.
Figure 4:
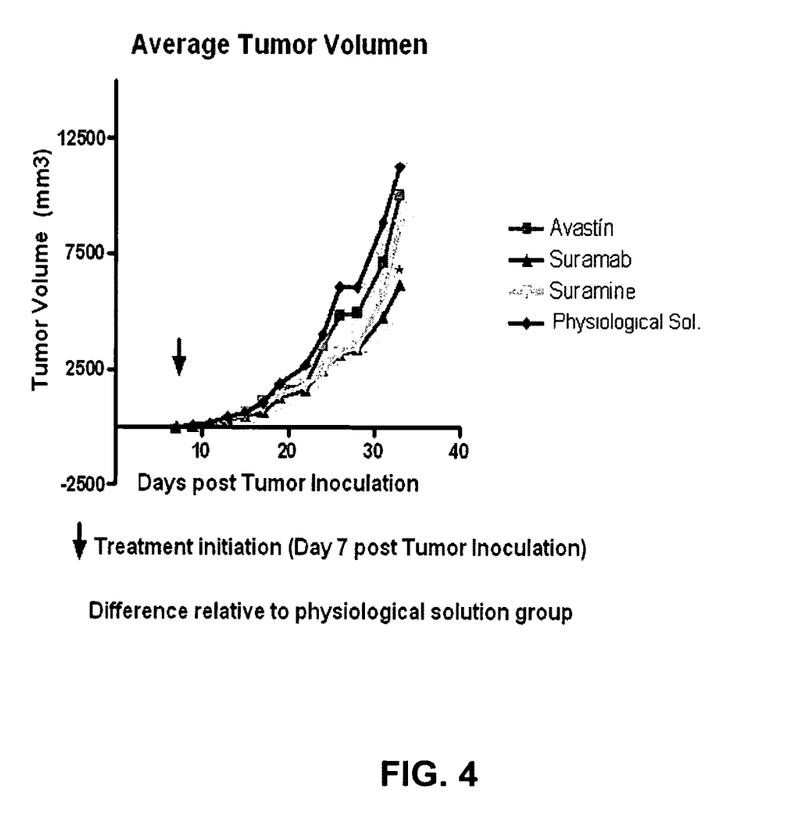
FIG. 4 shows the (average) tumor volume during the length of time (days) of the test of the oncological angiogenesis model for the four groups of animals up to day 31.
Figure 5:
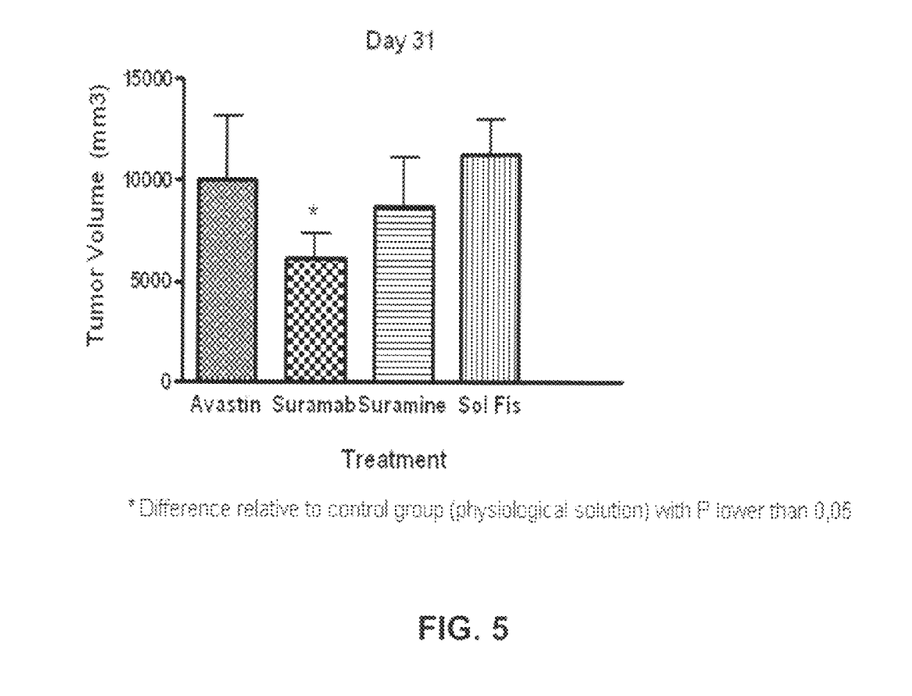
FIG. 5 illustrates the (average) tumor volume at day 31 of the test of oncological angiogenesis model for the four groups of animals.

As illustrated in FIGS. 3 through 5, the application of suramab has a significantly greater and synergistic effect on the degree of tumor volume growth (by inhibiting neovessels) at day 31 of evaluation (see FIGS. 4, 5) and a greater survival percentage at day 35 (see FIG. 3).

2.2.3.—Discussion and Conclusions

The present invention demonstrates that suramab is a provable effective agent to reduce corneal angiogenesis in a corneal neovasculizationun classical model (Bocci G, Danesi R, Benelli U, Innocenti F, Di Paolo A, Fogli S, Del Taca M. Inhibitory effect of suramin in rat models of angiogenesis in vitro and in vivo. Cancer Chemother Pharmacol 1999; 43 (3): 205-12; Zheng M, Schwarz M A, Lee S, Kumaraguru U, Rouse B T. Control of stromal keratitis by inhibition of neovascularization. Am J. Pathol. 2001 September; 159 (3): 1021-9). The degree of angiogenesis inhibition is significantly greater using suramab than using the treatment of only Bevacizumab or of Suramine. The noticeable difference was maintained during the complete period of evaluation.

The administered doses of each of suramab's component molecules (10 mg/kg Suramine+3 mg/kg Bevacizumab) is less than that administrated for Suramine (20 mg/kg) and Bevacizumab (5 mg/kg) singly. Half the doses, administrated combined, show a bigger effect and longer duration. Therefore, we have been able to notice a synergistic effect of the components of suramab. It seems reasonable to think that this synergy is based on the different action mechanism of Suramine (blocking cellular receptors) and Bevacizumab (binding to the circulating peptide).

We found a similar synergistic effect in the tests carried out with a tumor angiogenesis animal model using a different concentration of suramab. The doses administered of each of the compounding molecules of suramab (20 mg/kg Suramine+5 mg/kg Bevacizumab) is equal to that of Suramine (20 mg/kg) and Bevacizumab 5 mg/kg) administered singly. However a new doses, administered combined, showed a greater effect and duration.

The doses of Suramine used to develop suramab have been pointed out as non-toxic for the human organism (Villalona-Calero M A, Wientjes M G, Otterson G A, Kanter S, Young D, Murgo A J, Fisher B, DeHoff C, Chen D, Yeh T K, Song S, Greyer M, Au J L. Phase I Study of Low Dose suramin as a chemosensitizer in patients with advanced non-small cell lung cancer. Clin Cancer Res 2003; August 15; 9 (9): 3303-11) while the doses of Bevacizumab used with the same aim are those recommended for colon cancer patients (1996-2006, Productos Roche S.A.Q. e I., Buenos Aires).

Consequently, suramab could become a new alternative for treatment of oncological illnesses, at a time wherein different strategies are being discussed for the treatment of these illnesses (Schmoll H, Sargent D. Single agent fluorouracil for first-line treatment of advanced colorectal cancer as standard? Lancet 2007, 370: 105-107; Koopman M, Antonini N, Douma J, Wals J et al. Sequential versus combination chemotherapy with capecitabine, irinotecan, and oxaliplatin in advanced colorectal cancer (CAIRO): a phase Ill randomised controlled trial. Lancet 2007; 370: 135-42; Ramaswamy S. Rational design of cancer-drug combinations. NEJM 2007; 357 (3): 299-300; Seymour M, Maughan T, Ledermann J et al. Different strategies of sequential and combination chemotherapy for patients with poor prognosis advanced colorectal cancer (MR FOCUS): a randomised controlled trial. Lancet 2007; 370: 143-52).

Retinal pathological angiogenesis, as occurs in retinopathy of a premature baby, is an important cause of blindness in prematurely born children (Gallo J E, Lennerstrand G. A population-based study of ocular abnormalities in premature children aged 5 to 10 years. Am J Ophthalmol 1991 May 15; 111 (5): 539-47), initiating development of vitreo-retinal proliferation that generally leads to retinal detachment and later to blindness. A similar vitreo-retinal proliferation mechanism occurs in the final stage of diabetic retinopathy. These illnesses, as well as those that run their course with corneal neovascularization causing "blindness owing to the cornea", could benefit from treatment with suramab.

The current treatment of diabetic macular oedema, of proliferative diabetic retinopathy (con neovessels) and exudative-type macular degeneration is by means of an intravitrea injection (intravitreal) of an antiangiogenic drug, that must necessarily be repeated frequently in most cases (R. Lazic, N. Gabric. Verteporfin Therapy and Intravitreal Bevacizumab Combined and Alone in Choroidal Neovascularization due to Age-Related Macular Degeneration. Ophthalmology 2007, 114: (6), 1179-1185, Augustin A J, Puls S, Offermann I. Triple therapy for choroidal neovascularization due to age-related macular degeneration: verteporfin PDT, bevacizumab, and dexamethasone. Retina 2007; 27 (2):133-40, Yanyali A, Aytug B, Horozoglu F, Nohutcu A. Bevacizumab (Avastin) for diabetic macular edema in previously vitrectomized eyes. Am J Ophthalmol 2007; 144 (1):124-6, Arevalo F, Fromow-Guerra J, Quiroz-Mercado H, Sanchez J, Wu L, Maia M, Berrocal M, Solis-Vivanco A, Farah M, and Pan-American Collaborative Retina Study Group. Primary Intravitreal Bevacizumab (Avastin) for Diabetic Macular Edema. Results from the Pan-American Collaborative Retina Study Group at 6-Month Follow-up. Ophthalmology 2007, 114 (4) 743-750, Rabena M, Pieramici D, Castellarin A, Nasir M, Avery R. Intravitreal bevacizumab (Avastin) in the treatment of macular edema secondary to branch retinal vein occlusion. Retina 2007; 27 (4): 419-425). Considering the bigger effect and longer duration of suramab it would seem logical to expect reduction of frequency of these injections, with the advantage of diminishing the risk of contracting a severe intraocular infection (endophthalmitis) and of minimizing repetition of invasive processes on the patient.

Recent pieces of work on corneal neovascularization show how Bevacizumab (Avastin) administrated by parenteral and subconjuntivally means noticeably diminishes the presence of neovessels on the cornea (Bock F, Onderka J, Dietrich T, Bachmann B, Kruse F, Paschke M, Zahn G, Cursiefen C. Bevacizumab as a potent inhibitor of inflammatory corneal angiogenesis and lymphangiogenesis. Invest Ophthalmol V is Sci 2007; 48: 2545-2552; M Erdurmus and Totan Y. Subconjunctival bevacizumab for corneal neovascularization. Graefes Arch Clin Exp Ophthalmol 2007; doi 10.1007/s00417-007-0587-4). Still very preliminary results have been reported in topical administration (DeStafeno J, Kim T. Topical bevacizumab therapy for corneal neovascularization. Arch Ophthalmol 2007; 125: 834-836).

The objective of the investigation carried out was to evaluate suramab's effect (pharmaceutical composition comprising Suramine and Bevacizumab) in inhibiting corneal neovasculization and that associated to a cancer in two animal models. The results have certainly been very favourable.

The invention claimed is:

1. A synergistic pharmaceutical composition useful for inhibiting angiogenesis, in a human being or animal, comprising, in a pharmaceutically acceptable vehicle or carrier:
   60 to 90 weight % Suramin, or the equivalent of one of the pharmaceutically acceptable salts thereof; and
   40 to 10 weight % Bevacizumab;
   wherein weight % refers to the relative weight of Suramin and Bevacizumab in the composition.

2. The pharmaceutical composition according to claim 1, comprising in a pharmaceutically acceptable vehicle or carrier:
   approximately 75 weight % Suramin, or the equivalent of one of the pharmaceutically acceptable salts thereof; and
   approximately 25 weight % Bevacizumab;
   wherein weight % refers to the relative weight of Suramin and Bevacizumab in the composition.

3. The pharmaceutical composition according to claim 1, comprising:
   approximately 0.18 weight % Suramin, or the equivalent of one of the pharmaceutically acceptable salts thereof; and
   approximately 0.06 weight % Bevacizumab;
   the rest being a pharmaceutically acceptable vehicle or carrier, wherein the weight % refers to the relative weight of Suramin or Bevacizumab within the composition as a whole.

4. The pharmaceutical composition according to claim 1, comprises:
   approximately 0.18 weight % Suramin under the form of a hexa-sodium salt thereof; and
   approximately 0.06 weight % Bevacizumab;
   the rest being a pharmaceutically acceptable vehicle or carrier, wherein the weight % refers to the relative weight of Suramin or Bevacizumab within the composition as a whole.

5. The pharmaceutical composition according to claim 1, the composition being an injectable composition by intravenous, intravitrea or subconjuntival means or is for topical application.

* * * * *